United States Patent
Bruheim

(10) Patent No.: US 11,421,045 B2
(45) Date of Patent: Aug. 23, 2022

(54) KRILL-DERIVED CHITIN PRODUCTS AND METHODS OF MAKING SAME

(71) Applicant: RIMFROST TECHNOLOGIES AS, Fosnavag (NO)

(72) Inventor: Inge Bruheim, Volda (NO)

(73) Assignee: RIMFROST TECHNOLOGIES AS, Fostnavag (NO)

( * ) Notice: Subject to any disclaimer, the term of this patent is extended or adjusted under 35 U.S.C. 154(b) by 0 days.

(21) Appl. No.: 17/251,103

(22) PCT Filed: Jun. 11, 2019

(86) PCT No.: PCT/NO2019/050117
§ 371 (c)(1),
(2) Date: Dec. 10, 2020

(87) PCT Pub. No.: WO2019/240590
PCT Pub. Date: Dec. 19, 2019

(65) Prior Publication Data
US 2021/0189014 A1   Jun. 24, 2021

Related U.S. Application Data

(60) Provisional application No. 62/683,952, filed on Jun. 12, 2018, provisional application No. 62/827,492, filed on Apr. 1, 2019.

(51) Int. Cl.
*C08B 37/00* (2006.01)
*C08B 37/08* (2006.01)
*C12P 21/06* (2006.01)

(52) U.S. Cl.
CPC ........ *C08B 37/0003* (2013.01); *C08B 37/003* (2013.01); *C12P 21/06* (2013.01)

(58) Field of Classification Search
None
See application file for complete search history.

(56) References Cited

FOREIGN PATENT DOCUMENTS

| EP | 2334199 B1 | 6/2017 |
| WO | WO/2010/030193 | 3/2010 |

OTHER PUBLICATIONS

Chen, Journal of Aquatic Food Product Technology, vol. 26, Issue 10, 2017, abstract only. (Year: 2017).*
Chen, Journal of Aquatic Food Product Technology 2017, vol. 26, No. 10, 1210-1220. (Year: 2017).*
Harwood, FEMA Microbiology Reviews, fuab046, 46, 2022, 1-20. (Year: 2022).*
Brine, C. J. (1981) "Chitin variability with species and method of preparation," *Comparative Biochemistry and Physiology. B. Comparativebiochemistry* 69B(2), 283-286.
Chen, X. et al. (2017) "Recovery of Chitin from Antarctic Krill (Euphausia superba) Shell Waste by Microbial Deproteinization and Demineralization," *Journal of Aquatic Food Product Technology* 26(10), 1210-1220.
Jellouli, K. et al. (2011) "Alkaline-protease from Bacillus licheniformis MP1: Purification, characterization and potential application as a detergent additive and for shrimp waste deproteinization," *Process Biochemistry* 46(6), 1248-1256.
Nemtsev, S. V. et al. (2002) "Deacetylation of Chitin under Homogeneous Conditions," *Applied Biochemistry and Microbiology* 38(6), 521-526.
Rao, M. B. et al. (1998) "Molecular and Biotechnological Aspects of Microbial Proteases," *Microbiology and Molecular Biology Reviews* 62(3), 597-635.
Struszczyk, M. H. et al. (2002) "Chitin and chitosan," *Polimery (Warsaw)* 47(5), 316-325.
Wang, Y. et al. (2013) "Crystalline structure and thermal property characterization of chitin from Antarctic krill (Euphausia superba)," *Carbohydrate Polymers* 92(1), 90-97.
Yilmaz, B. et al. (2016) "Thermotolerant alkaline protease enzyme from Bacillus licheniformis A10: purification, characterization, effects of surfactants and organic solvents," *Journal of Enzyme Inhibition and Medicinal Chemistry* 31(6), 1241-1247.
Younes, I. et al. (2015) "Chitin and chitosan preparation from marine sources. Structure, properties and applications," *Marine Drugs* 13(3), 1133-1174.
Zhang, Y. et al. (2006) "Preparation of half-deacetylated chitosan by forced penetration and its properties," *Carbohydrate polymers.* 65(3), 229-234.
PCT International Search Report of International Application No. PCT/NO2019/050117 dated Oct. 9, 2019.

* cited by examiner

*Primary Examiner* — Layla D Berry
(74) *Attorney, Agent, or Firm* — Medlen & Carroll, LLP

(57) ABSTRACT

Methods of producing a chitin composition by which the properties of the chitin composition derived from krill, such as molecular weight (chain length) and degree of acetylation are reproducible, are claimed. Such reproducible production methods allow for a wide use of the chitin composition end products in pharmaceutical and biomedical applications. The methods also allow for the production of chitin compositions which preserve the native state of chitin.

59 Claims, 1 Drawing Sheet

First Hydrolysis
Krill Shell Preparation
Second Hydrolysis
Extract Chitin
Chitin Composition

KRILL-DERIVED CHITIN PRODUCTS AND METHODS OF MAKING SAME

BACKGROUND OF THE INVENTION

The present invention relates to the art of providing purified chitin compositions, and in particular, to deriving highly purified chitin compositions from krill shells.

The biopolymer chitin or poly ($\beta$-(1→4)-N-acetyl-d-glucosamine) is a natural polysaccharide of major importance. Chitin is synthesized by myriad living organisms and is one of the most abundant of natural polymers, after cellulose. In its native state, chitin occurs as ordered crystalline microfibrils which form structural components in the exoskeleton of arthropods or in the cell walls of fungi and yeast. The main commercial sources of chitin are crab and shrimp shells. In industrial processing, chitin is extracted by acid treatment to dissolve the calcium carbonate followed by alkaline solution to dissolve proteins. Typically, a decolorization step is added. These treatments must be adapted to the chitin source, due to differences in the initial material, to produce a chitin product, and then, after deacetylation, a chitosan product. The lack of solubility of chitin is a major problem in its processing, use and characterization.

Since chitin is a natural polymer, as well as biocompatible and biodegradable in the body, it can be used for biomedical and pharmaceutical applications. Examples include drug release and wound dressing. Additionally, good film forming properties of chitin may be valuable for biofilms, artificial skin and packaging.

In the past methods to perform enzymatic hydrolysis of Antarctic krill has been described. It has been shown that krill shells can be separated from the hydrolyzed matrix of krill. However, the shells are not processed further. Due to the water content, the products are not microbiologically stable and have a low value. Typically, they are discarded after production. There is a need to utilize all the fractions from krill from an economical and environmental perspective.

Krill shells have in the past also been defatted and used for extraction of chitin. The yield of chitin product obtained from defatted krill shell was 27.80±1.48%. This results in a low overall yield and poor commercial potential.

However, up to now, a reproducible quality of chitin has been difficult to obtain. The lack of standardized product has inhibited the full potential of therapeutic applications of chitin, in particular, in the biomedical and/or pharmaceutical fields.

Therefore, there remains a need for improved methods to isolate chitin from krill in a cost-effective, fast and easily controllable industrial process for producing chitin having high purity, high crystallinity index, and high molecular weight.

SUMMARY OF THE INVENTION

The present invention provides production methods by which the properties of chitin compositions derived from krill are reproducible. For example, properties, such as molecular weight (chain length) and degree of acetylation are reproducible. Such reproducible production methods allow for a wide use of the chitin composition end products in pharmaceutical and biomedical applications. The methods also allow for the production of chitin compositions which preserve the native state of chitin.

One aspect of the invention relates to a method of producing a chitin composition wherein deacetylation and depolymerization of krill chitin is minimized, the method including: a) deproteinizing a krill product to provide a deproteinized krill product; and b) isolating the chitin composition, wherein the chitin composition is at least about 30% to about 99% acetylated, and wherein the average molecular weight of the krill chitin is about 300 kDa to about 800 kDa, about 400 kDa to about 700 kDa, or about 400 kDa to about 600 kDa. Preferably, the krill product comprises whole krill. The method may preferably further include demineralizing the krill product to provide a demineralized krill product. The demineralizing step may be performed before the deproteinizing step.

The chitin composition may have a Crystallinity Index (CI) of greater than about 80%, greater than about 85%, or greater than about 90%. The average molecular weight of the krill chitin may be about 400 kDa to about 600 kDa. In one preferred embodiment, the chitin composition has a crystallinity index (CI) between about 85% and about 95%, and the average molecular weight of the krill chitin is about 400 kDa to about 600 kDa. In a preferred embodiment, the chitin composition is at least 90% homogenous.

Another aspect of the invention relates to a bioactive krill-chitin composition prepared by the process including the steps of: a) deproteinizing a krill product to provide a deproteinized krill product; and b) isolating the bioactive krill-chitin composition, wherein the chitin composition is at least about 95% acetylated and wherein the average molecular weight of the chitin composition is about 300 kDa to about 800 kDa, about 400 kDa to about 700 kDa, or about 400 kDa to about 600 kDa.

The bioactive krill-chitin composition may also be prepared with an additional demineralizing step where the krill product is demineralized to provide a demineralized krill product. In a preferred embodiment, the bioactive krill-chitin composition has a Crystallinity Index (CI) of greater than about 80%.

Another aspect of the invention relates to a method of producing a chitin composition, the method including: a) a first enzymatic hydrolysis of a krill product to produce hydrolyzed krill; b) separating the solid portion of the hydrolyzed krill; c) chemical deproteinization and chemical demineralization of the solid portion to produce a chitin composition; and d) providing a chitin composition comprising i) crystallinity index (CI) is greater than about 85%; ii) a purity of greater than about 80%; and iii) average molecular weight of about 300 kDa to about 700 kDa.

In one embodiment, the first enzymatic hydrolysis including contacting with a metalloprotease. In another embodiment, the first enzymatic hydrolysis further includes contacting with a first protease mixture. In a preferred embodiment, the first enzymatic hydrolysis includes contacting with a first protease mixture; and contacting with a second protease mixture. In another preferred embodiment, the method includes a second enzymatic hydrolysis including contacting with a first protease mixture. The first enzymatic hydrolysis may include one or more of acid protease, neutral protease, and alkaline proteases.

The first protease mixture may include at least one alkaline protease; and the second protease mixture may include an acid protease, a neutral protease, and an alkaline protease. The first protease mixture may include 0.3-0.5% of the total weight of the disintegrated crustacean catch; and the second protease mixture may include 0.03-0.05% of the total weight of the disintegrated crustacean catch. In a preferred embodiment, the proteases are from *Bacillus licheniformis*. The first enzymatic hydrolysis may include contacting with a cell wall degrading enzyme. Preferably, the chemical deproteinization occurs before the demineralization.

Preferably, the solid portion of the hydrolyzed krill includes between about 10% and about 25% lipids, and between about 35% and about 55% protein. Also, preferably, the solid portion of the hydrolyzed krill includes between about 13% and about 18% lipids, and between about 40% and about 50% protein.

Chemical deproteinization may include exposing the solid portion to NaOH. The NaOH may have a molar concentration of about 1M to about 4M. Chemical deproteinization may occur at about 80° C. Chemical deproteinization may last about 1 to about 7 days or about 1 to about 4 days.

Demineralization may include exposing the solid portion to HCl. The HCl may have a molar concentration of about 1M. Demineralization may occur at about 95° C. Demineralization may last about 30 minutes.

In any of the processing steps, it is preferred that the temperature does not exceed 60° C., 70° C., 75° C., 80° C., 85° C., 90° C., 95° C., or 100° C.

The preferred crystallinity index (CI) of the chitin composition is greater than about 85%, greater than about 90%, or greater than about 95%. Preferably, the crystallinity index (CI) of the chitin composition is between about 85% and about 95%.

Preferably, the chitin composition includes a total amount of trace minerals of less than 5 ppm, less than 1 ppm, and less than 0.1 ppm. Preferably, the individual amounts of trace minerals include less than 5 ppm, less than 1 ppm, and less than 0.1 ppm. The trace minerals may include iron, calcium, phosphorus, magnesium, potassium, zinc, nickel, selenium, and copper.

Preferably, the chitin composition is at least 90%, at least 95%, or at least 99% pure. Also, preferably, the chitin composition is at least 90% homogenous.

Another aspect of the invention relates to a chitin composition having a crystallinity index of greater than 80%; a molecular weight of less than 700 kDa; and a purity of greater than 90%. Preferably, the chitin composition is a krill chitin composition.

The chitin composition preferably has a crystallinity index (CI) greater than about 85%, greater than about 90%, or greater than about 95%. Preferably, the chitin composition has a crystallinity index (CI) between about 85% and about 95%.

Also, preferably, the chitin composition is at least 90%, at least 95%, or at least 99% pure. Most preferably, the chitin composition is substantially free of impurities. Impurities may include proteins, lipids, trace minerals, and combinations thereof. Substantially free means containing less than 10%, less than 5%, or less than 1% impurities. In a preferred embodiment, the chitin composition includes a total amount of trace minerals of less than 5 ppm, less than 1 ppm, and less than 0.1 ppm. Preferably, the individual amounts of trace minerals comprise less than 5 ppm, less than 1 ppm, and less than 0.1 ppm. The trace minerals may include iron, calcium, phosphorus, magnesium, potassium, zinc, nickel, selenium, and copper.

In a preferred embodiment, the chitin composition includes less than 10% protein, less than 5% protein, less than 1% protein, or less than 0.1% protein. In another preferred embodiment, the chitin composition includes less than 10% lipid, less than 5% lipid, less than 1% lipid, or less than 0.1% lipid.

Preferably, the chitin composition comprises an average molecular weight of between about 300 kDa to about 800 kDa, about 400 kDa to about 700 kDa, or about 400 kDa to about 600 kDa.

Another aspect of the invention relates to a chitin composition having a crystallinity index of between about 80% and about 90%; an average molecular weight of between about 400 kDa and about 600 kDa; and a purity of between about 90% and about 98%.

DESCRIPTION OF THE DRAWINGS

FIG. 1 is a flow chart showing the steps of isolating a chitin composition from a raw material such as a krill product. The first step involves a first hydrolysis. The second step involves krill shell preparation. The third step involves a second hydrolysis. The fourth step involves extraction of chitin to product a chitin composition.

DETAILED DESCRIPTION OF THE INVENTION

Chitin, found in krill shells, is a constituent of a complex network with proteins (i.e., a polysaccharide-protein complex) onto which trace minerals deposit to form a rigid shell.

In one aspect, the present invention provides methods to remove protein and other deleterious components (e.g., fluoride) from chitin derived from krill shells and preserving the native structure of chitin (e.g., molecular weight and degree of acetylation).

Since the methods of the present invention substantially preserve the native state of krill chitin, the end products are reproducible and predictable. For example, properties, such as molecular weight (chain length) and degree of acetylation are reproducible. Such reproducible production methods allow the end product krill chitin compositions to be used in pharmaceutical/biomedical applications which typically require standardization.

The present invention also provides analytical methods by which to determine total and extractable chitin in krill; and the strength and nature of bonding between the chitin and proteins in krill.

In one aspect, the present invention provides environmentally sustainable methods to extract chitin from krill that preserve molecular specificities in the final product. In one embodiment, such methods can be performed onboard a shipping vessel, such as, for example, a krill harvesting vessel.

Throughout this specification, quantities are defined by ranges, and by lower and upper boundaries of ranges. Each lower boundary can be combined with each upper boundary to define a range. The lower and upper boundaries should each be taken as a separate element.

Krill Product

Any variety of krill can be used in the invention. The preferred krill is Antarctic krill (*Euphausia superba*). The use of *Euphausia pacifica* is also contemplated. The krill can also be whole krill, krill powder, or krill meal. The whole krill can be fresh or previously frozen. However, fresh whole krill caught within 60 minutes, more preferably within 30 minutes is preferred. Krill powder is made by any method known in the art.

In one embodiment, the krill product is produced by way of the methods described in EP2334199B1.

In one embodiment, the krill product is produced by contacting a disintegrated krill with a first protease mixture and a second protease mixture.

Disintegrating Crustacean Catch

The crustacean catch is disintegrated (immediately in the case of freshly caught krill) in order to form a disintegrated crustacean catch. Disintegrating involves mechanically breaking apart the crustacean catch into smaller pieces or smaller particle sizes to be more conducive for subsequent processing steps. The following values may be combined in any manner to create a minima, a maxima, or a range for the particle sizes of the disintegrated crustacean catch: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, and 25 mm. For example, the disintegrated crustacean catch may have particles sizes of between approximately 1-25 mm, more preferably between approximately 3-15 mm, and most preferably between approximately 3-6 mm.

The crustacean catch may be disintegrated using any conventional means to effectuate a particular range of particle sizes. For example, the disintegration apparatus may grind, pulp, mill, and/or shred the crustacean catch. Examples of disintegration apparatus include, but are not limited to, a knife shredder, a blender, and a homogenizer.

The temperature at which the disintegration process takes place is around the ambient temperature of the water in which the crustacean catch was caught when the crustacean catch is fresh, e.g, krill caught within 60 minutes. Therefore the temperature would be between about −2° C. and about +1° C., preferably about 0° C. to about +6° C.

Hydrolysis

The second step involves contacting the disintegrated crustacean catch with one or more proteolytic enzymes to provide a hydrolyzed crustacean catch. A hydrolyzed crustacean catch is formed when the disintegrated crustacean catch undergoes hydrolysis. Hydrolysis is a chemical reaction or process which can be caused or mediated by a biological agent, such as a proteolytic enzyme, whereby the natural protein sequences become shorter (i.e., for example, by breaking peptide bonds of the amino acid sequence primary structure) to form smaller peptides and free amino acids.

The disintegrated crustacean catch needs to be hydrolyzed so that digestive enzymes such as lipase and phospholipase which are released from the crustacean catch upon death may be inactivated. If these digestive enzymes are not inactivated upon their release, then they will destroy the phospholipids and fatty acids within the crustacean catch. In order to inactivate the digestive enzymes, the disintegrated crustacean catch is contacted with a proteolytic enzyme under certain conditions to form a hydrolyzed crustacean catch. The proteolytic enzyme is chosen specifically to target the digestive enzymes with minimally damaging the other proteins within the krill which may be utilized downstream while separating some phospholipid and peptides from the exoskeletons of the disintegrated crustacean catch.

Conditions of hydrolysis such as choice of enzyme, temperature, pH, and duration are chosen to attain a partially hydrolyzed crustacean catch with a specific degree of hydrolysis. A partially hydrolyzed catch is preferred so the digestive enzymes may be inactivated while other proteins may be broken down into smaller peptides and free amino acids. By contrast, a fully hydrolyzed crustacean catch, which is not preferred, would mean that all of the proteins within the catch would be broken down into free amino acids.

Degree of hydrolysis may be determined by methods known in the art such as pH-stat, trinitrobenzenesulfonic acid (TNBS), o-phthaldialdehyde (OPA), trichloroacetic acid soluble nitrogen (SN-TCA), and formol titration methods. The following percentages may be combined to create a range or be used individually as minima or maxima to specify the degree of hydrolysis 10%, 15%, 20%, 25%, 30%, 35%, 40%, 45%, 50%, 55%, 60%, 65%, 70%, 75%, 80%, 85%, 90%, 95%, 96%, 97%, 98%, and 99%. For example, greater than about 30% of the protein in the crustacean catch is hydrolyzed. More preferably, greater than about 40% of the protein in the crustacean catch is hydrolyzed. In another embodiment, the degree of hydrolysis may be up to 90% to specify that the hydrolysis is almost complete.

Furthermore, partially hydrolyzed proteins by their nature increase digestibility of the proteins. For example, the pepsic digestibility of the partially hydrolyzed proteins may be roughly about 85%, 86%, 87%, 88%, 89%, 90%, 91%, 92%, 93%, 94%, or 95%. Most preferably, the pepsic digestibility of the partially hydrolyzed proteins is about 91%. Increased digestibility means that partially hydrolyzed proteins are nutritious for animals that are unable to synthesize the essential amino acids. There is interest in using the partially hydrolyzed protein by products as a feed supplement for aquatic species and/or pets.

Pepsic digestibility may be measured by standard practices in vivo or by newer practices conducted in vitro. Previously, researchers would determine pepsic digestibility in vivo using rat, rooster, and/or chicken subjects to measure the amount of digested protein when the animal was fed a protein-containing compound. Animal feces would be analyzed for nitrogen-content which would provide an indication of the amount of digestible protein in the product. Newer methods of determining protein digestibility can be conducted in vitro by adding a spectroscopic agent to the hydrolyzed protein solution that reacts with the amine functional group or the carboxylic acid functional group so that the amount of amino acid released during enzymatic digestion may be optically evaluated.

Additionally, the proteolytic enzyme(s), conditions, and duration of hydrolysis are specifically chosen to inactivate the digestive enzymes without substantially denaturing any of the proteins within the krill including the digestive enzymes and other proteins (the proteins apart from the digestive enzymes). Denaturing occurs when the protein loses its quaternary, tertiary, and/or secondary structure which is present in its native state.

In another embodiment, either the digestive enzymes are not denatured or the other proteins are not denatured. Partially hydrolyzed proteins that have not been denatured are preferable because they have been found to retain substantial amounts of water in a form that is unavailable for biological growth up to 2, 3, 4, 5, 6, 7, 8, 9, or 10 times longer than protein that has been denatured which retains less water in a form unavailable for biological growth. The ability to hold water increases the utility of the PPC by increasing flowability and storability of the product. Therefore, it would be advantageous for the PPC or any other downstream product containing the partially hydrolyzed proteins to be able to hold a substantial amount of water without promoting biological growth for a longer period of time.

Without substantially denaturing the other proteins is defined as 0%, less than 1%, less than 2%, less than 3%, less than 4%, less than 5%, less than 6%, less than 7%, less than 8%, less than 9%, less than 10%, less than 20%, less than 25%, or less than 30% denaturing of the other proteins within the krill.

Hydrolysis preferably occurs when the disintegrated crustacean catch is contacted with the proteolytic enzyme and incubated. The optimal temperature of incubation is the temperature to activate the particular enzyme(s) which is conducive for hydrolysis of the digestive enzymes without denaturing the other proteins within the crustacean catch. The temperature can be achieved during processing by any means known in the art. Preferably, the proteolytic enzyme is added to hot water and then mixed with the disintegrated crustacean catch under agitation.

Alternatively, the proteolytic enzyme may be added to water and then the mixture may be heated, or the enzyme, water, and disintegrated crustacean catch are mixed together and then heated.

The following percentage values may be combined to create a minima, a maxima, or a range for the amount of water added during the contacting step based upon the weight of the disintegrated catch: 35%, 36%, 37%, 38%, 39%, 40%, 41%, 42%, 43%, 44%, 45%, 46%, 47%, 48%, 49%, 50%, 51%, 52%, 53%, 54%, and 55%. For example, water is added in an amount of up to about 50% of the weight of the disintegrated catch. In another example, about 45% to about 50% of water is added based upon the weight of the disintegrated catch.

The following values may be combined to create a minima and maxima or a range for the temperatures under which the disintegrated crustacean catch is optimally hydrolyzed, i.e., incubated: 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., and 75° C. For example, the contacting step includes incubating the disintegrated crustacean catch at a temperature range of about 45° C. to about 75° C. These temperatures may apply to the temperature of the water or the temperature of the mixture of water, enzyme(s), and/or disintegrated crustacean catch. For example, the water may be heated up to temperatures of about 60° C. before being mixed with the proteolytic enzyme(s). In another example, the enzyme(s) may function optimally at about 45° C. to about 65° C.

The quantity of enzyme used may be determined by a person having ordinary skill in the art to inactivate enough of the digestive enzymes without substantially denaturing the other proteins within the krill and to separate some phospholipid and peptides from the exoskeletons of the disintegrated crustacean catch.

For example, the proteolytic enzyme may be used in a quantity less than about 0.1% of the total weight of the disintegrated crustacean catch. The following values may be combined in any manner to create a range with a minima and a maxima for the quantity of proteolytic enzyme as a percentage of the total weight of the disintegrated crustacean catch: 0.3%, 0.29%, 0.28%, 0.27%, 0.26%, 0.25%, 0.24%, 0.23%, 0.22%, 0.21%, 0.2%, 0.19%, 0.18%, 0.17%, 0.16%, 0.15%, 0.14%, 0.13%, 0.12%, 0.11%, 0.1%, 0.09%, 0.08%, 0.07%, 0.06%, 0.05%, 0.04%, 0.03%, 0.02%, and 0.01%. In one embodiment, the proteolytic enzyme may be used in step b) in a quantity of about 0.01% to 0.1% based upon the total weight of the disintegrated crustacean catch.

The pH of the solution may be adjusted to ensure that hydrolysis proceeds optimally based upon the particular proteolytic enzyme(s) being used.

The hydrolysis step may take any reasonable time to produce a hydrolyzed crustacean catch. Factors affecting the time required for hydrolysis include the temperature and pH of the mixture as well as whether the reaction takes place with or without agitation and the intensity of the agitation.

For example, hydrolysis may take less than 100 minutes. The following values in minutes may be combined in any manner to create a range with a minima and maxima for time necessary for hydrolysis: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. As an example, hydrolysis may take about 15-18 minutes, or hydrolysis may take less than about 45 minutes.

In another embodiment, hydrolysis may take over 100 minutes. The following values in minutes may be combined in any manner to create a range with a minima and maxima for time necessary for hydrolysis: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, and 240. As an example, hydrolysis may take about 100-180 minutes, or hydrolysis may take less than about 180 minutes.

Proteolytic Enzymes

The proteolytic enzymes useful in the present invention are food grade enzymes that cleave large protein molecules into smaller molecules by hydrolyzing peptide bonds along the protein backbone. As used herein, the term "proteolytic enzyme", "protease", and "peptidase" are used interchangeably. As used herein, the term "exopeptidase" refers to a hydrolase enzyme that removes terminal amino acids of a peptide or protein by cleaving peptide bonds. A terminal amino acid is an amino acid that is within about 10 amino acids of the N-terminus or C-terminus of a protein or peptide. As used herein, the term "endopeptidase" refers to an enzyme that catalyzes the cleavage of peptide bonds within a polypeptide or protein. Peptidase refers to the fact that it acts on peptide bonds and endopeptidase refers to the fact that these are internal bonds.

Proteolytic enzymes include, but are not limited to, esterase enzymes such as carboxylic-ester hydrolases, thioester hydrolases, phosphoric-monoester hydrolases, phosphatases, phosphoric-diester hydrolases, triphosphoric-monoester hydrolases, sulfuric-ester hydrolases, sulfatases, diphosphoric monoesterases, and phosphoric-triester hydrolases; Glycosylases, such as glycosidases, i.e., enzymes that hydrolyse O- and S-glycosyl compounds and those that hydrolyse N-glycosyl compounds; Enzymes that act on ether bonds such as hydrolysing thioether and trialkylsulfonium; peptidases include exopeptidases such as aminopeptidases, dipeptidyl-peptidases and tripeptidyl-peptidases, carboxypeptidases (serine-type carboxypeptidases, metallocarboxypeptidases, cysteine-type carboxypeptidases), dipeptidases, omega peptidases, and peptidyl-dipeptidases, and endopeptidases such as serine endopeptidases, cysteine endopeptidases, aspartic endopeptidases, metalloendopeptidases such as Corolase® 7089 from Ab Enzymes, CAS 9001-92-7, and threonine endopeptidases; enzymes that hydrolyse carbon-halide compounds in a single sub-subclass; enzymes that act on phosphorus-nitrogen bonds; Enzymes that act on sulfur-nitrogen bonds; enzymes that hydrolyse C-phosphono-groups; Enzymes that act on sulfur-sulfur bonds; and enzymes that act on carbon-sulfur bonds.

In one embodiment, protease mixtures may be used. Suitable protease mixtures include one or more of acid, neutral, or alkaline proteases.

Acid proteases are protein-digesting enzymes that exhibit maximum activity and stability in acid conditions (e.g., pH 2.0-5.0, 2.0-3.0, 2.0-4.0, or 3.0-5.0) and are inactivated at pH values above 6.0. Acid proteases generally have a low isoelectric point and have a low basic amino acid content.

Neutral proteases are active in a narrow pH range (pH 5 to 8) and may have relatively low thermotolerance. Neutral proteases include cysteine proteases, metalloproteases, and some of the serine proteases.

Alkaline proteases are characterized by their high activity at alkaline pH, e.g., at least pH 9, at least pH 10, at least pH 11. Examples of alkaline proteases include serine proteases. They have broad substrate specificities including esterolytic and amidase activity. The isoelectric points of serine proteases are generally between pH 4 and 6. Serine alkaline proteases that are active at highly alkaline pH represent the largest subgroup of serine proteases.

In one embodiment, the protease mixture includes proteases from *Bacillus licheniformis*. Acid, neutral, and alkaline proteases from *Bacillus licheniformis* are known in the art. See for example, Yilmaz et al., J Enzyme Inhib Med Chem, 2016, 31(6):1241-1247; Rao et al., Microbiology and Molecular Biology Reviews, 1998, 62(3): 597-635; and Jellouli et al., Process Biochemistry, 2011, 46(6): 1248-1256.

In one embodiment, the protease mixture includes a food grade cell wall degrading enzyme obtained from the organisms from the genus *Aspergillus*. Examples of cell wall degrading enzymes from *Aspergillus* include mylase, pectinase, xylanase, and cellulose enzymes. Specific examples include β-glucosidase, endoglucanase, filterpaperase, polygalacturonase, and pectate lyase.

In one embodiment, the method of the present invention includes addition of a first protease mixture having at least one alkaline protease; and a second protease mixture having at least one of an acid protease, a neutral protease, and an alkaline protease.

The first protease mixture includes at least one, at least two, at least three, or at least four alkaline protease. In one embodiment, the alkaline protease(s) is from *Bacillus licheniformis*. In one embodiment, the first protease mixture includes only endoproteases.

In one embodiment, the first protease mixture includes one alkaline protease.

In one embodiment, the first protease mixture includes two alkaline proteases. In one embodiment, the first alkaline protease and second alkaline protease total 100% of the proteases of the first protease mixture. In one embodiment, the first alkaline protease is 1-80% of the protease mixture and the second alkaline protease is 1-80% of the protease mixture. In one embodiment, the first alkaline protease is 1-30% of the protease mixture and the second alkaline protease is 70-99% of the protease mixture. In one embodiment, the first alkaline protease is 1-10% of the protease mixture and the second alkaline protease is 9-99% of the protease mixture. In one embodiment, the first alkaline protease and second alkaline protease are present in equal proportions in the first protease mixture.

In one embodiment, the first protease mixture includes three alkaline proteases. In one embodiment, the first alkaline protease, second alkaline protease, and the third alkaline protease total 100% of the proteases of the first protease mixture. In one embodiment, the first alkaline protease is 1-80% of the protease mixture, the second alkaline protease is 1-80% of the protease mixture, and the third alkaline protease is 1-80% of the protease mixture. In one embodiment, the first alkaline protease is 1-30% of the protease mixture, the second alkaline protease is 1-30% of the protease mixture, and the third alkaline protease is 50-98% of the protease mixture. In one embodiment, the first alkaline protease is 1-10% of the protease mixture, second alkaline protease is 1-30% of the protease mixture, and the third alkaline protease is 10-98% of the protease mixture. In one embodiment, the first alkaline protease, second alkaline protease, and third alkaline protease are present in equal proportions in the first protease mixture.

The second protease mixture includes at least one of: acid protease, a neutral protease, and an alkaline protease. In one embodiment, the acid protease, neutral protease, or alkaline protease are from *Bacillus licheniformis*. The proteases of the second protease mixture may include exoproteases and endoproteases.

In one embodiment, the second protease mixture includes an acid protease and a neutral protease. In one embodiment, the acid protease and neutral protease total 100% of the proteases of the second protease mixture. In one embodiment, the second protease mixture includes 1-80% acid protease and 1-80% neutral protease. In one embodiment, the acid protease is 1-30% of the protease mixture and the neutral protease is 70-99% of the protease mixture. In one embodiment, the acid protease is 1-10% of the protease mixture and neutral protease is 9-99% of the protease mixture. In one embodiment, the acid protease and neutral protease are present in equal proportions in the second protease mixture.

In one embodiment, the second protease mixture includes an acid protease and an alkaline protease. In one embodiment, the acid protease and alkaline protease total 100% of the proteases of the second protease mixture. In one embodiment, the second protease mixture includes 1-80% acid protease and 1-80% alkaline protease. In one embodiment, the acid protease is 1-30% of the protease mixture and the alkaline protease is 70-99% of the protease mixture. In one embodiment, the acid protease is 1-10% of the protease mixture and the alkaline protease is 9-99% of the protease mixture. In one embodiment, the acid protease and alkaline protease are present in equal proportions in the second protease mixture.

In one embodiment, the second protease mixture includes a neutral protease and an alkaline protease. In one embodiment, the first neutral protease and alkaline protease total 100% of the proteases of the second protease mixture. In one embodiment, the second protease mixture includes 1-80% neutral protease and 1-80% alkaline protease. In one embodiment, the neutral protease is 1-30% of the protease mixture and the alkaline protease is 70-99% of the protease mixture. In one embodiment, the neutral protease is 1-10% of the protease mixture and the alkaline protease is 9-99% of the protease mixture. In one embodiment, the neutral protease and alkaline protease are present in equal proportions in the second protease mixture.

In one embodiment, the second protease mixture includes an acid protease, a neutral protease, and an alkaline protease. In one embodiment, the acid protease, neutral protease, and alkaline protease total 100% of the proteases of the second protease mixture. In one embodiment, the second protease mixture contains 1-80% acid protease, 1-80% neutral protease, and 1-80% alkaline protease. In one embodiment, the second protease mixture contains 1-10% acid protease, 1-30% neutral protease, and 60-98% alkaline protease. In one embodiment, the acid protease, neutral protease, and alkaline protease are present in equal proportions in the second protease mixture.

In one embodiment, the alkaline protease of the first protease mixture is not in the second protease mixture.

In one embodiment, the amount of first protease mixture/second protease mixture is 0.2-0.6% first protease mixture and 0.02-0.06% of the second protease mixture. In one embodiment, the amount of first protease mixture/second protease mixture is 0.3-0.5% first protease mixture and 0.03-0.05% of the second protease mixture. In one embodiment, the amount of first protease mixture is about 0.4% and the amount of second is about 0.04%.

A preferred commercially available protease mixture for the first protease mixture includes Endocut-02L (TailorFood/Tailorzyme). A preferred commercially available protease mixture for the second protease mixture includes Exocut-BL (TailorFood/Tailorzyme). Exocut-BL may include a cell wall degrading enzyme from *Aspergillus*, instead of or in addition to one or more protease.

The following values may be combined in any manner to create a range with a minima and maxima for the quantity of Exocut protease mixture as a percentage of the total weight of the disintegrated crustacean catch: 0.005%, 0.01%, 0.02%, 0.03%, 0.04%, 0.05%, 0.06%, 0.07%, 0.08%, 0.09%, 0.1%, 0.25%, or 0.5%.

In one embodiment, the amount of Endocut/Exocut is 0.2-0.6% Endocut protease mixture and 0.02-0.06% of the Exocut protease mixture. In one embodiment, the amount of Endocut/Exocut is 0.3-0.5% Endocut protease mixture and 0.03-0.05% of the Exocut protease mixture. In one embodiment, the amount of Endocut is about 0.4% and the amount of Exocut is about 0.04%.

In one embodiment, the first protease mixture and second protease mixture are simultaneously added to the disintegrated crustacean catch.

In one embodiment, the hydrolysis step includes contacting the crustacean catch with the first protease mixture prior to contacting the crustacean catch with the second protease mixture. In this embodiment, the following values in minutes may be combined in any manner to create a range with a minima and maxima for time necessary for hydrolysis with the first protease mixture, prior to the addition of the second protease mixture: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, and 240. For example, the disintegrated crustacean catch is hydrolyzed for 1-10 minutes with the first protease mixture prior to the addition of the second protease mixture.

In one embodiment, the hydrolysis step includes contacting the second protease mixture with the disintegrated crustacean catch prior to contacting the crustacean catch with the first protease mixture. In this embodiment, the following values in minutes may be combined in any manner to create a range with a minima and maxima for time necessary for hydrolysis with the second protease mixture, prior to the addition of the first protease mixture: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, and 240. For example, the disintegrated crustacean catch is hydrolyzed for 1-10 minutes with the second protease mixture prior to the addition of the first protease mixture. In another embodiment, a second enzyme comprising chitinase or collagenase is used. This enzyme may be used in combination with a first enzyme or enzyme combination.

In another embodiment, the enzyme(s) used in hydrolysis do not contain an exopeptidase.

The contacting step may also include the use of an organic solvent. Examples of useful organic solvents include, but are not limited to, ethanol, acetone, and ethylacetate.

Stopping Hydrolysis

Hydrolysis may be stopped by inactivating the enzyme(s). The enzyme(s) may be deactivated in different ways including adding inhibitors, removing co-factors (e.g. crucial ions through dialysis), through thermal inactivation, and/or by any other deactivating means.

Conditions whereby each enzyme is inactivated may vary, but normally include raising the pH and temperature of the solution. For example, deactivation of Corolase® 7089 begins at pH values >7.5 and temperatures greater than 55° C. The conditions are chosen so that the enzyme is inactivated at temperatures that will not denature the protein from the disintegrated crustacean catch. The following temperatures may be combined in any manner to create a minima, a maxima, or a range for the temperatures under which the enzyme(s) is inactivated without denaturing the protein from the crustacean catch: 85° C., 86° C., 87° C., 88° C., 89° C., 90° C., 91° C., 92° C., 93° C., 94° C., 95° C., 96° C., 97° C., 98° C., 99° C., and 100° C. For example, enzyme A may be inactivated at a temperature over about 90° C. or preferably between about 92° C. and about 98° C.

As discussed above, hydrolysis is stopped at the correct moment so that the crustacean catch is preferably only partially hydrolyzed to produce a hydrolyzed crustacean catch wherein the proteins have a specified degree of hydrolysis. Furthermore, a person having ordinary skill in the art would be able to ascertain the conditions and duration of hydrolysis with specific enzyme(s) and conditions to produce a hydrolyzed crustacean catch wherein a certain percentage of the crustacean catch is hydrolyzed.

Second Hydrolysis Step

Chitin can be extracted from krill using conventional methods such as the ones described above. However, it has been found that lipids interfere with the process. In the krill material tested there were a significant amount of total lipids that were remaining (they were weighted at 16% of raw weight). They influence significantly the extraction process. A saponification process has been noted during the deproteinization phase. Upon analysis, it has been determined to be the result of a cross reaction that is occurring while the chemistry attacks the proteins and releases phosphorus that reacts with some lipids to create phospholipidic complexes. They will force the mixture to form a kind of gel (it is actually very similar to a toothpaste), hence forcing the agitation rate to increase of seeing the extraction efficiency to go down. This gel is very sensitive to temperature. Its viscosity increases with increase of temperature, to a point where we can lose control of the batch at some point.

Proteins are the key factor to focus on when it comes to extract chitin from the krill material. Chitin binding from krill seems stronger with proteins than with minerals, to the contrary of shrimp or crab shell. And some lipids are strongly related to those proteins. If we eliminate too much lipids beforehand, there is a chance we remove part of the chitin/protein complexes that are a whole part of the krill. If we have too much lipids, then we form a gel during the extraction process. This gel limits the temperature at which we can operate the extraction. It also complicates dramatically the liquid/solid separation out of the process reactors, which has an impact on final purity.

It has been unexpectedly discovered that a second hydrolysis step increases the yield of chitin and increases the crystallinity index.

In one embodiment, a second hydrolysis step using the first protease mixture described above is performed on the krill product described above.

The following values may be combined in any manner to create a range with a minima and maxima for the quantity of first protease mixture as a percentage of the total weight of the processed krill product for extraction of chitin: 0.01%, 0.02%, 0.03%, 0.04%, 0.05%, 0.06%, 0.07%, 0.08%, 0.09%, 0.1%, 0.2%, 0.3%, 0.4%, or 0.5%.

The following values may be combined in any manner to create a range with a minima and maxima for the quantity of Endocut protease mixture as a percentage of the total weight of the disintegrated crustacean catch: 0.01%, 0.1%, 0.2%, 0.3%, 0.4%, 0.5%, 0.6%, 0.7%, 0.8%, 0.9%, 1.0%, or 1.5%.

In this embodiment, the following values in minutes may be combined in any manner to create a range with a minima and maxima for time necessary for hydrolysis in the second hydrolysis step: 30, 31, 32, 33, 34, 35, 36, 37, 38, 39, 40, 45, 50, 55, 60, 65, 70, 75, 80, 85, 90, 95, 100, 105, 110, 115, or 120. For example, the disintegrated crustacean catch is hydrolyzed for 50-80 minutes or 55-65 minutes with the first protease mixture.

The following values may be combined to create a minima and maxima or a range for the temperatures under second hydrolysis step, i.e., incubated: 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., and 75° C. For example, the temperature range of about 45° C. to about 75° C., about 45° C. to about 60° C., or about 50° C. to about 60° C. These temperatures may apply to the temperature of the water or the temperature of the mixture of water, enzyme(s), and/or processed krill product for extraction. For example, the water may be heated up to temperatures of about 55° C. or about 60° C. before being mixed with the proteolytic enzyme(s). In another example, the enzyme(s) may function optimally at about 50° C. to about 60° C.

In one embodiment, water is added to the processed krill product for extraction of chitin at about 1:1.5, 0.07% to 0.2% first protease mixture at a temperature range of about 50° C.-60° C.

Isolating Chitin Composition

Isolating a chitin composition includes a deproteinization step and a demineralization step.

Deproteinization Preserving Native Structure of Krill Chitin

Chitin content in krill is typically about 12-16% of the krill weight. Deproteinization of krill includes the disruption of chemical bonds between chitin and proteins thereby allowing the separation of proteins from the chitin.

The invention provides methods of deproteinization by which the native structure of krill chitin is substantially preserved. The molecular weight (MW) of krill chitin is about 250-350 kDa. Krill chitin is of α-type and high crystallinity level (about 90%).

In one respect, the native krill chitin structure is preserved is by minimizing, or completely avoiding, deacetylation and depolymerization of the chitin during deproteinization. For example, at least about 50% to about 99% of the chitin is acetylated. Examples of other lower boundaries of this range include about 55%, about 60%, about 65%, about 70%, and about 75%. Examples of other upper boundaries of this range include about 80%, about 85%, about 90%, about 95% and about 98%. For example, the average molecular weight of the chitin composition is about 300 kDa to about 400 kDa, or about 400 kDa to about 600 kDa. Examples of other lower boundaries of this range include about 300 kDa, about 325 kDa, about 340 kDa, about 350 kDa, and about 375 kDa. Examples of other upper boundaries of this range include about 300 kDa, about 325 kDa, about 350 kDa, about 375 kDa, about 380 kDa, about 400 kDa, about 500 kDa, and about 800 kDa.

In one embodiment, the chitin product is at least 80%, at least 90%, at least 95%, or at least 99% homogenous. By way of example, a chitin product is 99% homogenous when 99% of the chitin product is of a specified characteristic (or range of a particular characteristic), including MW, deacetylation, purity, or crystallinity index.

Also, in some embodiments, terpenes (e.g., astaxanthin and canthaxanthin) are also included in the end product chitin compositions.

Such preservation of native structure and nutritional elements allows for the production of a reproducible chitin composition end product, which reproducibility is important for biomedical and pharmacological applications.

Chemical Deproteinization involves treating krill with one or more deproteinization reagents which include, but are not limited to, $NaOH$, $Na_2CO_3$, $NaHCO_3$, $KOH$, $K_2CO_3$, $Ca(OH)_2$, $Na_2SO_3$, $NaHSO_3$, $CaHSO_3$, $Na_3PO_4$, and $Na_2S$. In addition to deproteinization, the use of chemicals reagents, particularly at the higher ends of concentration, temperature and time, results in partial deacetylation of chitin and hydrolysis of the biopolymer lowering its molecular weight, i.e., thereby disrupting the native chitin structure.

However, in some embodiments of the invention, deproteinization using chemical reagents under mild conditions and/or low concentrations can be combined with another deproteinization method. For example, concentrations of the chemical reagents do not exceed about 0.5M, temperatures do not exceed about 50° C., and duration of treatment does not exceed about one hour. For instance, 0.3M NaOH at 25° C. for 45 minutes can allow for deproteinization while minimizing deacetylation and depolymerization.

In one embodiment, enzymatic hydrolysis may occur on previously frozen krill to produce a hydrolyzed krill product. The hydrolyzed krill product is run through a decanter or sedecanter to separate the shells (solid phase) from the soluble portions (liquid phase). The shells may then be dried and undergo chemical deproteinization with one of the bases listed above.

The solid phase or solid portion of the hydrolyzed krill includes the following amounts of lipids, minimum or maximum amount of lipids, or a range of lipids made using the values: 10%, 11%, 12%, 13%, 14%, 15%, 16%, 17%, 18%, 19%. 20%, 21%, 22%, 23%, 24%, and 25%, based upon the total percent of the solid portion. For example, the solid portion of the hydrolyzed krill may include between about 10% and about 25% lipids or between about 13% to about 18% lipids.

The solid phase or solid portion of the hydrolyzed krill includes the following amounts of protein, minimum or maximum amount of protein, or a range of protein made using the values: 35%, 36%, 37%, 38%, 39%, 40%, 41%, 42%, 43%, 44%. 45%, 46%, 47%, 48%, 49%, 50%, 51%, 52%, 53%, 54%, and 55%, based upon the total percent of the solid portion. For example, the solid portion of the hydrolyzed krill made include between about 35% and about 55% protein or between about 40% and about 50% protein.

For example, chemical deproteinization may occur using NaOH in a concentration of, minimum or maximum concentration of, or range of concentrations of the following values: 1M, 2M, 3M, 4M, or 5M; at an elevated temperature of, minima or maxima or range of the following values: 50° C., 55° C., 60° C., 65° C., 70° C., 75° C., 80° C., 85° C., 90°

C., 95° C., and 100° C.; for a duration of, or minimum period or maximum period or range of the following values: 6 hours, 12 hours, 18 hours, 24 hours, 2 days, 3 days, 4 days, 5 days, 6 days, 7 days, 8 days, 9 days, and 10 days.

Demineralizing Krill

In some embodiments of the invention, the krill may be demineralized to remove calcium carbonate by chemical or biological means. Demineralizing krill is preferably performed by exposing the krill to acid treatment. Examples of demineralization agents include, but are not limited to, HCl, $HNO_3$, $H_2SO_4$, $CH_3COOH$, and HCOOH. The preferred agent is dilute HCl. The acid reacts to decompose the calcium carbonate to form water-soluble calcium salts, water, and carbon dioxide. Other minerals present in the krill react similarly and form soluble salts in the presence of acid. The salts are removed by filtration and washing with water. The acid, concentration, duration, and temperature of the demineralization process can be determined by a person having ordinary skill in the art. An example of typical conditions is 3.5% HCl at 20° C. for 1.5 hours to demineralize krill.

For example, the demineralization acid may be HCl at a concentration of, minimum concentration of, maximum concentration of, or range of concentrations of the following values: 0.1M, 0.2M, 0.3M, 0.4M, 0.5M, 0.6M, 0.7M, 0.8M, 0.9M, 1 M, 1.1M, 1.2M, 1.3M, 1.4M, and 1.5M, 2M, 2.5M, 3M, 3.5M, 4M, 4.5M, and 5M. The temperature of the demineralization may be at an elevated temperature of, or minima or maxima or range of the following values: 60° C., 65° C., 70° C., 75° C., 80° C., 85° C., 90° C., 95° C., 100° C., 105° C., and 110° C. The duration of the demineralization may be a duration of, minimum period of, a maximum period of, or a range of the following values: 10 minutes, 15 minutes, 20 minutes, 25 minutes, 30 minutes, 35 minutes, 40 minutes, 45 minutes, 50 minutes, 55 minutes, and 60 minutes.

In one embodiment, demineralization conditions include 0.5M-2.0M HCl, at 80° C.-100° C. for 20 to 45 minutes. In one embodiment, the demineralization step may occur with 1M HCl at 90° C. for 30 minutes.

In one embodiment, the shell was treated with 1.7 M HCl at an ambient temperature for 6 h and then with 2.5 M NaOH at 75° C. for 1 h.

The pigments may be decomposed by using 1% potassium permanganate. The purified chitin product is lyophilized.

In one embodiment, the final chitin product has no trace minerals. In another embodiment, the final chitin product has less than 5 ppm, 4 ppm, 3 ppm, 2 ppm, 1 ppm, 0.9 ppm, 0.8 ppm, 0.7 ppm, 0.6 ppm, 0.5 ppm, 0.4 ppm, 0.3 ppm, 0.2 ppm, or 0.1 ppm trace minerals. Trace minerals include iron, calcium, phosphorus, magnesium, potassium, zinc, nickel, selenium, and copper.

In one embodiment, demineralization is performed before deproteinization. By performing demineralization prior to deproteinization, the subsequent chitin composition is more pure, shorter, and loss of final chitin as mass, as compared to performing deproteinization before demineralization.

In one embodiment, deproteinization is performed before demineralization.

Lipid Removal

A lipid removal step may optionally be used to "polish" the isolated chitin. Any method of lipid removal may be used, such as, extraction with an organic solvent such as ethanol or methanol. The ethanol or methanol may be removed from the extract by evaporation. The resulting polished chitin is clear white.

Crystallinity Index

Crystallinity index (CI) refers to the proportion of material present in the crystalline state. In other words, CI is a quantitative indicator of crystallinity. Generally, the crystallinity of chitin and its oligomer can be evaluated using X-ray diffraction measurements. The peak intensity of chitin is recorded over the scattering range of 4.5° to 50° with scan steps of 0.02° at a speed of 4.0° $min^{-1}$ The CI is generally measured by a method, which uses a maximum intensity of 110 (I110) and the intensity of amorphous halo contribution (Iam) as follows:

$$CI=((I110-Iam)/I110)\times100 \qquad (7)$$

The crystallinity index provides an idea on the crystalline fraction in chitin and its derivatives.

The CI of the chitin product may be adjusted to attain a higher CI. For example, the CI of synthesized samples may be dependent upon the acid/alkali concentrations. For example, higher crystallinity may be achieved with the use of moderate alkali concentration and low acid concentration. In another example, the CI may be increased by oxidizing with concentrated HCl the amorph regions of the molecule.

The process of the present invention provides a krill chitin having a CI of at least 80, 85, 90, or 95, without the need for additional crystallization or re-crystallization steps or processes.

Preferably, CI is greater than the following values or the following values may be used to create a range for the CI: about 80, 81, 82, 83, 84, 85, 86, 87, 88, 89, 90, 91, 92, 92, 93, 94, or 95. For example the CI is greater than about 85, the CI is greater than about 90, or the CI is greater than about 95. In another example, the CI is between about 85 and about 95.

Purity

The purity of the final chitin product is at least 90%, 91%, 92%, 93%, 94%, 95%, 96%, 97%, 98%, or 99% pure. Preferably, the chitin composition is at least 90%, at least 95%, or at least 99% pure. Impurities may include protein, lipids, and minerals. By way of example, a chitin composition according to the claimed invention having 95% purity means that the composition includes 95% chitin and 5% of protein, lipids, minerals, and combinations thereof.

Krill-Derived Chitin Composition End Products

The use of krill shells for the production of end products provides advantages compared to other marine sources in that krill does not contain synthetic components, such as, for example, antibiotics.

For biomedical/pharmaceutical uses, the complete removal of protein from the chitin is important, since a substantial percentage of the human population is allergic to shellfish protein. Unlike state of the art methods, the deproteinization methods of the present invention substantially preserve the native state of krill chitin; thus the end products are reproducible and predictable. For example, properties, such as molecular weight (chain length) are degree of acetylation (DA) are reproducible. Such reproducible production methods allow the chitin composition end products to be used in pharmaceutical biomedical applications which typically require standardization.

In one embodiment, present invention provides pharmaceutical compositions comprising a) the krill-derived chitin compositions produced by the methods of the present invention and b) pharmaceutical carriers or excipients. The pharmaceutical compositions of the invention can be formulated per se in pharmaceutical preparations, or with a suitable pharmaceutical carrier (vehicle) or excipient, as understood by practitioners in the art.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums, and glycols.

In one embodiment, present invention provides food additives comprising the krill-derived chitin compositions produced by the methods of the present invention.

In one embodiment, present invention provides biomedical devices comprising the krill-derived chitin compositions produced by the methods of the present invention. Examples of such devices include wound dressing, biofilms, artificial skin, packaging, and vaccine adjuvants.

In one embodiment, the present invention provides chitin for use in the preparation of nanocrystals.

In one embodiment, the present invention provides a decolorization step of the chitin. Decolorization may be achieved by soaking chitin in 1% oxalic acid for at least 10 minutes, at least 20 minutes, or at least 30 minutes. In another embodiment, the soaking is done for a maximum of 45 minutes, 1 hour, 2 hours, 4 hours, or 24 hours. The decolorization may be done at any stage of chitin processing or isolation described above.

EXAMPLES

Example 1

Frozen Antarctic krill (*Euphausia superba*) was thawed and subjected to an enzymatic hydrolysis process as described in WO2010/030193. The krill shells were isolated using a decanter and the contents were analyzed. The results are shown in Table 1.

TABLE 1

Composition of the krill shells.

| Parameter | Content |
| --- | --- |
| Lipids | 16.2% |
| Proteins | 45.7% |
| Ash | 21.4% |
| Chitin | 13.7% |
| Water | 3.1% |

The shells were dried and used as a raw material for a chitin extraction process. Four different isolation procedures were conducted as shown below in Table 2.

TABLE 2

Process for the isolation of the chitin from the krill shells.

| Sample ID# | First | Second |
| --- | --- | --- |
| 1 | 1M NaOH, 80° C., 24 h | 1M HCl, 95° C., 30 min. |
| 2 | 2M NaOH, 80° C., 7 days | 1M HCl, 95° C., 30 min. |
| 3 | 4M NaOH, 80° C., 7 days | 1M HCl, 95° C., 30 min. |
| 4 | 1M HCl, 95° C., 30 min. | 1M NaOH, 80° C., 24 h |

Results

| Sample ID# | % Protein | % Chitin | % Lipids | Crystallinity index | Yield |
| --- | --- | --- | --- | --- | --- |
| 1 | 0 | 84.6 | 15.4 | 82 | 21.5 |
| 2 | 0 | 82.4 | 17.6 | 82 | 13.0 |
| 3 | 0 | 82.5 | 17.5 | 84 | 18.9 |
| 4 | 0 | 97.1 | 2.9 | 85 | 15.6 |

Commercial chitin has a Crystallinity Index of about 75%. The final chitin products have no trace minerals, i.e., mineral content is less than 1 ppm.

Example 2

Example 2A—Hydrolysis of Krill

Krill shells were prepared according to EP2334199B1. A dry matter of 40% was obtained and the shells were dried.

TABLE 3 dry matter composition of dried shells.

| Lipids | 5.2% |
| --- | --- |
| Protein | 21% |
| Chitin | 18.3% |
| Ash | 40.2% |

Example 2B—Hydrolysis of Krill Using Multiple Enzymes

Frozen krill was lyophilized and its shell was separated. A dry matter of 40% were obtained and the shells were dried.

The enzymatic hydrolysis was done be using food grade enzymes Endocut and Exocut (obtained from Tailorzymes) in combination and at a level of about 0.4% and about 0.04%, respectively. Temperature of 55° C. and reaction time of about 2 hours.

TABLE 4

| Lipids | 23% |
| --- | --- |
| Protein | 10.8% |
| Chitin | 37.6% |
| Ash | 19.2% |

Example 2C—Double Hydrolysis/Re-Hydrolysis

The material from example 2B were added water (1:1.5) and 0.1% Endocut, mixture was incubated at 55° C. for 1 hour.

TABLE 5 based upon dry matter.

| Lipids | 13.9% |
| --- | --- |
| Protein | 22.1% |
| Chitin | 44.8% |
| Ash | 19.2% |

Example 2D—Extraction of Chitin from Material from Examples 2A and 2B

Chitin was extracted from the krill shells obtained in example 2A and example 2B using chemical demineralization and chemical deproteinization, as described above.

TABLE 6 summary of characteristics of the extracted chitin.

|  | 2A | 2C |
|---|---|---|
| Yield | 60% | 80% |
| Crystallinity Index | 85% | 85% |
| Purity | 95% | 95% |
| MW | 650 kDa | 650 kDa |

What is claimed is:

1. A method of producing a chitin composition, said method comprising:
   a) a first enzymatic hydrolysis and a second enzymatic hydrolysis of a krill product to produce a hydrolyzed krill product;
   b) separating a solid portion of said hydrolyzed krill product;
   c) deproteinizing and demineralizing said hydrolyzed krill product solid portion under mild conditions with at least one chemical to produce a chitin composition;
   wherein said chitin composition comprises; i) a crystallinity index (CI) that is greater than about 85; ii) a purity of greater than 80%; and iii) an average molecular weight of between 300 kDa-700 kDa; and wherein said first enzymatic hydrolysis is performed for 1 to 240 minutes.

2. The method of claim 1, wherein said first enzymatic hydrolysis comprises contacting said krill product with a metalloprotease.

3. The method of claim 1, wherein said first enzymatic hydrolysis comprises contacting said krill product with a first protease mixture.

4. The method of claim 1, wherein said first enzymatic hydrolysis comprises contacting said krill product with a second protease mixture.

5. The method of claim 1, wherein said solid portion of said hydrolyzed krill product comprises between 10%-25% lipids and between 35%-55% protein.

6. The method of claim 1, wherein said method is maintained at a temperature selected from the group consisting of 60° C., 70° C., 75° C., 80° C., 85° C., 90° C., 95° C., and 100° C.

7. The method of claim 1, wherein said chitin composition comprises a crystallinity index (CI) selected from the group consisting of greater than 90% and greater than 95%.

8. The method of claim 1, wherein said second enzymatic hydrolysis comprises contacting said krill product with a first protease mixture.

9. The method of claim 3, wherein said first protease mixture comprises at least one alkaline protease.

10. The method of claim 4, wherein said second protease mixture comprises at least one of an acid protease, a neutral protease, and an alkaline protease.

11. The method of claim 8, wherein said first protease mixture comprises an alkaline protease.

12. The method claim 1, wherein said second hydrolysis is performed for 30 to 120 minutes.

13. The method of claim 2, wherein said metalloproteinase is a metallocarboxypeptidase or a metalloendopeptidase.

14. The method of claim 1, wherein said first hydrolysis is performed before or after said second hydrolysis.

15. The method of claim 1, wherein said first hydrolysis further comprises a cell wall degrading enzyme.

16. The method of claim 3, wherein said first protease mixture is between 0.3-0.5% of the total weight of said hydrolyzed krill product.

17. The method of claim 3, wherein said first protease mixture comprises at least one protease from *Bacillus licheniformis*.

18. The method of claim 3, wherein said first protease mixture consists of endoproteases.

19. The method of claim 3, wherein said first protease mixture consists of alkaline proteases.

20. The method of claim 3, wherein said first protease mixture is selected from the group consisting of 1-80% alkaline proteases, 1-30% alkaline proteases and 1-10% alkaline proteases.

21. The method of claim 3, wherein said first protease mixture comprises a first alkaline protease and a second alkaline protease.

22. The method of claim 21, wherein said first protease mixture consists of said first alkaline protease and said second alkaline protease.

23. The method of claim 21, wherein said first protease mixture comprises 1-80% of said first alkaline protease and 1-80% of said second alkaline protease.

24. The method of claim 21, wherein said first protease mixture comprises 1-30% of said first alkaline protease and 70-99% of said second alkaline protease.

25. The method of claim 21, wherein said first protease mixture comprises 1-10% of said first alkaline protease and 9-99% of said second alkaline protease.

26. The method of claim 21, wherein said first alkaline protease and second alkaline protease are present in equal proportions.

27. The method of claim 21, wherein said first protease mixture comprises a first alkaline protease, a second alkaline protease and a third alkaline protease.

28. The method of claim 27, wherein said first protease mixture consists of said first alkaline protease, said second alkaline protease and said third alkaline protease.

29. The method of claim 27, wherein said first protease mixture comprises 1-80% of said first alkaline protease, 1-80% of said second alkaline protease, and 1-80% of said third alkaline protease.

30. The method of claim 27, wherein said first protease mixture comprises 1-30% of said first alkaline protease, 1-30% of said second alkaline protease, and 50-98% of said third alkaline protease.

31. The method of claim 27, wherein said first protease mixture comprises 1-10% of said first alkaline protease, 1-30% of said second alkaline protease, and 10-98% of said third alkaline protease.

32. The method of claim 27, wherein said first alkaline protease, said second alkaline protease, and said third alkaline protease are present in equal proportions.

33. The method of claim 3, wherein said first protease mixture as a percentage of the total weight of said hydrolyzed krill product is selected from the group consisting of 0.01%, 0.02%, 0.03%, 0.04%, 0.05%, 0.06%, 0.07%, 0.08%, 0.09%, 0.1%, 0.2%, 0.3%, 0.4%, or 0.5%.

34. The method of claim 4, wherein said first protease mixture is added simultaneously with said second protease mixture.

35. The method of claim 4, wherein said first protease mixture is added between 1-10 minutes prior to said second protease mixture.

36. The method of claim 4, wherein said second protease mixture comprises between 0.03-0.05% of the total weight of said krill product.

37. The method of claim 4, wherein said second protease mixture comprises at least one protease from *Bacillus licheniformis*.

38. The method of claim 4, wherein said second protease mixture comprises exoproteases and endoproteases.

39. The method of claim 4, wherein said second protease mixture comprises an acid protease and a neutral protease.

40. The method of claim 39, wherein said second protease mixture comprises between 1-80% of said acid proteases and 1-80% of said neutral proteases.

41. The method of claim 39, wherein said second protease mixture comprises between 1-30% of said acid proteases and 70-99% of said neutral proteases.

42. The method of claim 39, wherein said second protease mixture comprises between 1-10% of said acid proteases and 9-99% of said neutral proteases.

43. The method of claim 39, wherein said second protease mixture comprises said acid proteases and said neutral proteases in equal proportions.

44. The method of claim 4, wherein said second protease mixture comprises an alkaline protease and a neutral protease.

45. The method of claim 44, wherein said second protease mixture comprises between 1-80% of said alkaline proteases and 1-80% of said neutral proteases.

46. The method of claim 44, wherein said second protease mixture comprises between 1-30% of said alkaline proteases and 70-99% of said neutral proteases.

47. The method of claim 44, wherein said second protease mixture comprises between 1-10% of said alkaline proteases and 9-99% of said neutral proteases.

48. The method of claim 44, wherein said second protease mixture comprises said alkaline proteases and said neutral proteases in equal proportions.

49. The method of claim 4, wherein said second protease mixture comprises an acid protease, a neutral protease, and an alkaline protease.

50. The method of claim 4, wherein said second protease mixture consists of acid proteases, neutral proteases, and alkaline proteases.

51. The method of claim 50, wherein said second protease mixture is selected from the group consisting of 1-80% of said acid proteases, 1-80% of said neutral proteases, and 1-80% of said alkaline proteases.

52. The method of claim 50, wherein said second protease mixture is selected from the group consisting of 1-10% acid proteases, 1-30% neutral proteases, and 60-98% alkaline proteases.

53. The method of claim 10, wherein said acid proteases, said neutral proteases, and said alkaline proteases are present in equal proportions.

54. The method of claim 34, wherein the amount of said first protease mixture is between 0.2-0.6% and the amount of said second protease mixture is between 0.02-0.06%.

55. The method of claim 34, wherein the amount of said first protease mixture is between 0.3-0.5% and the amount of said second protease mixture is 0.03-0.05%.

56. The method of claim 34, wherein the amount of said first protease mixture is about 0.4% and the amount of said second protease mixture is about 0.04%.

57. The method of claim 35, wherein the amount of said first protease mixture is between 0.2-0.6% and the amount of said second protease mixture is between 0.02-0.06%.

58. The method of claim 35, wherein the amount of said first protease mixture is between 0.3-0.5% and the amount of said second protease mixture is 0.03-0.05%.

59. The method of claim 35, wherein the amount of said first protease mixture is about 0.4% and the amount of said second protease mixture is about 0.04%.

\* \* \* \* \*